(12) United States Patent
Schumaier

(10) Patent No.: US 7,614,867 B2
(45) Date of Patent: Nov. 10, 2009

(54) EARPLUG SHAPER AND METHOD OF USE

(76) Inventor: Daniel R. Schumaier, 1548 Blue Springs Rd., Elizabethton, TN (US) 37643

( * ) Notice: Subject to any disclaimer, the term of this patent is extended or adjusted under 35 U.S.C. 154(b) by 493 days.

(21) Appl. No.: 11/391,051

(22) Filed: Mar. 28, 2006

(65) Prior Publication Data
US 2007/0227546 A1    Oct. 4, 2007

(51) Int. Cl.
*B29C 59/02* (2006.01)
(52) U.S. Cl. ............... 425/402; 264/320; 181/130; 128/864; 128/867
(58) Field of Classification Search ........... 425/402; 264/320; 181/130; 128/864, 867
See application file for complete search history.

(56) References Cited

U.S. PATENT DOCUMENTS

| | | | |
|---|---|---|---|
| 378,406 A * | 2/1888 | Kugler | 37/403 |
| 4,053,051 A | 10/1977 | Brinkhoff | |
| 4,219,018 A | 8/1980 | Draper, Jr. | |
| 5,195,539 A * | 3/1993 | Dyrud et al. | 128/864 |
| 5,322,185 A | 6/1994 | Leight | |
| D378,406 S | 3/1997 | Kugler | |
| 5,609,164 A * | 3/1997 | Dyrud et al. | 128/864 |

OTHER PUBLICATIONS

Tweezerman Website (obtained from internet archive) archived Feb. 7, 2005. The Slant (R) tweezer page. http://www.tweezerman.com/scripts/item.cfm?gc=B&sc=TZ&itemsku=1231T&topmenu=1&submenu=1 is the current web page.*

* cited by examiner

*Primary Examiner*—Kat Wyrozebski
*Assistant Examiner*—Robert J Grun
(74) *Attorney, Agent, or Firm*—Luedeka, Neely & Graham, P.C.

(57) ABSTRACT

An earplug shaping device shapes a compressible earplug prior to insertion of the earplug into a user's ear canal. The device includes upper and lower structural elements which slidingly engage one another. Each of the upper and lower structural elements include a shaping surface. The shaping surfaces oppose one another and are inclined relative to one another. Various embodiments of the earplug shaper employ a slot in communication with a receiver which allows for the shaping of earplugs attached to a cord.

14 Claims, 5 Drawing Sheets

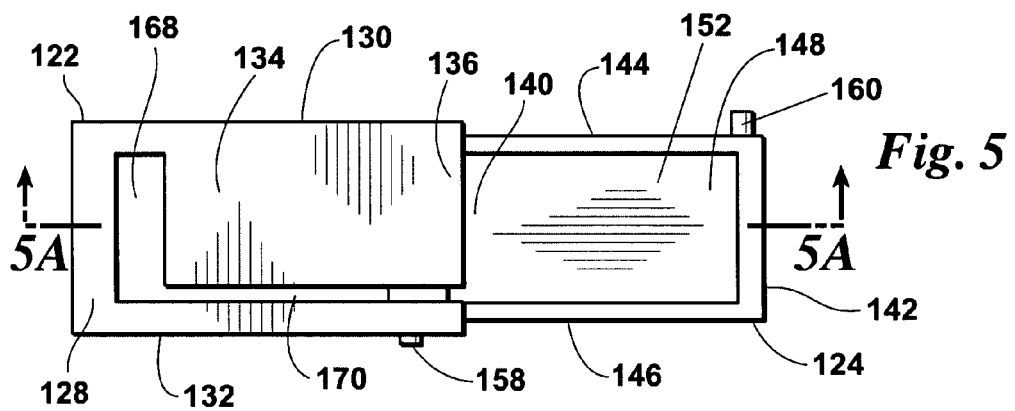
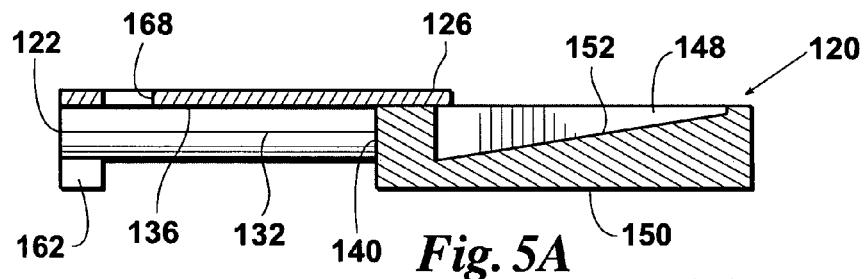
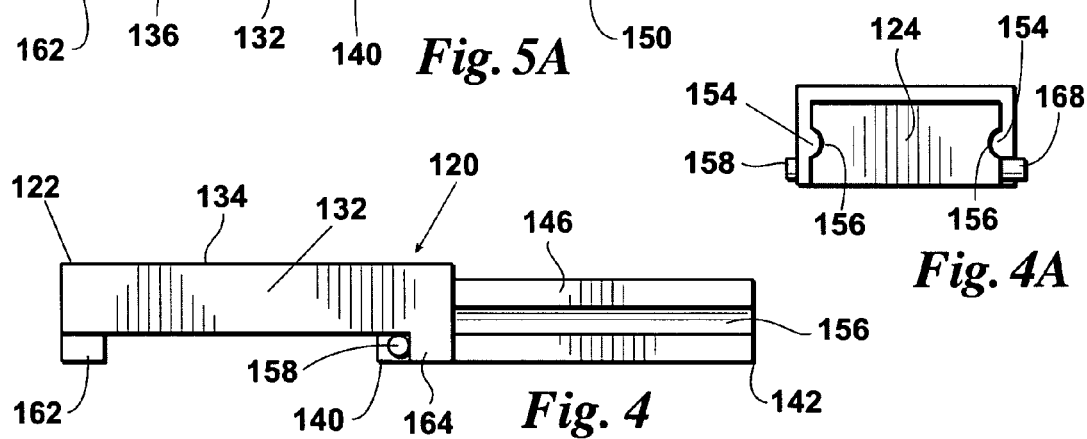
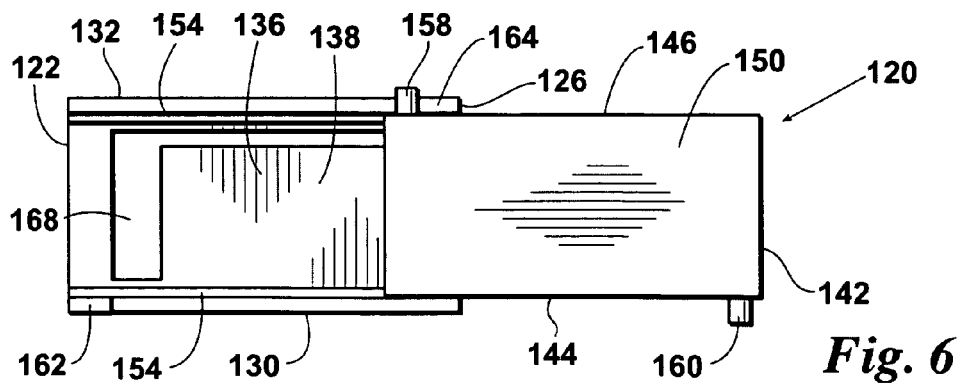

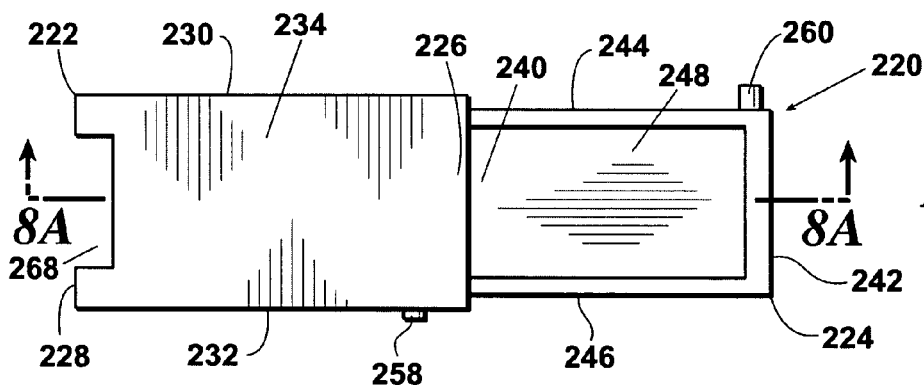
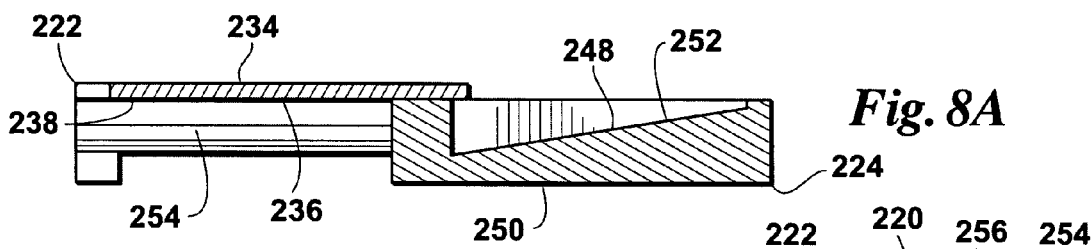
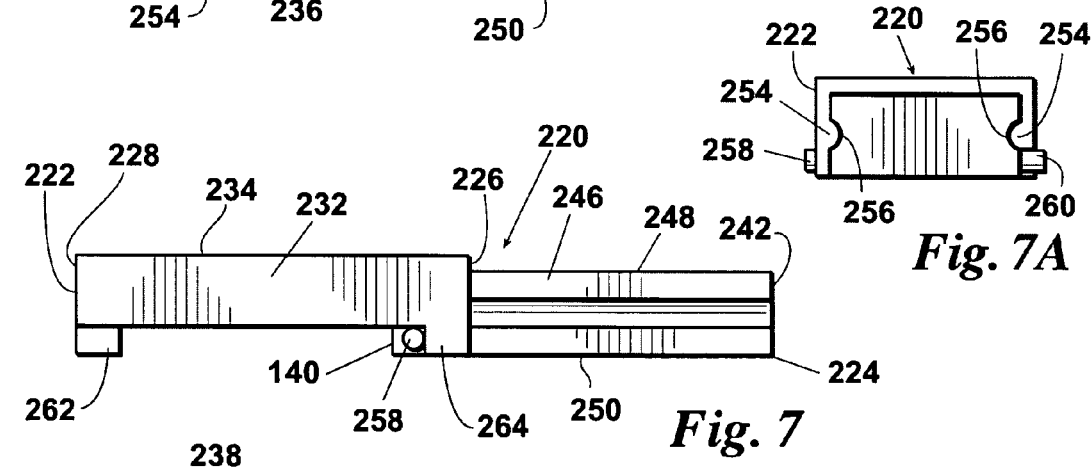
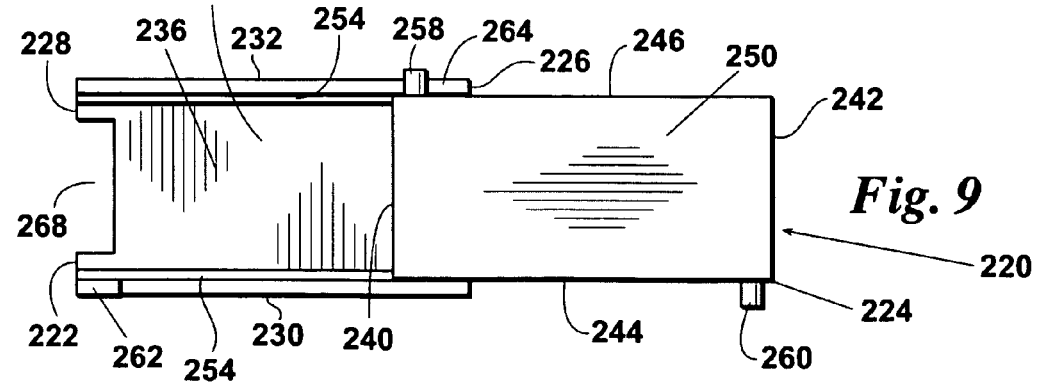

EARPLUG SHAPER AND METHOD OF USE

1. FIELD OF THE INVENTION

The present invention relates generally to earplug shaping devices. More particularly, the present invention relates to a device uniquely configured to uniformly shape PVC, polyethylene and other resilient/slow recovery earplugs to a proper pre-insertion diameter to enhance effective use of the earplugs.

2. BACKGROUND OF THE INVENTION

In manufacturing, construction and other noisy environments, continued exposure to high sound levels can cause hearing loss. Repeated exposure to noise levels above 90 decibels can cause hearing loss in a relatively short time. Hearing loss has become such a problem in the United States that OSHA requires any workers who are continually exposed to an ambient noise level above 90 decibels to wear hearing protection.

Hearing loss arising out of continued exposure to high sound levels can easily be avoided or greatly reduced by the use of hearing protection devices, such as earmuffs or earplugs. Earmuffs typically have a cup or shell which fits over the top of the ear with padding in between the shell and the user's head which helps seal out noise. While earmuffs generally work well, they are typically awkward to wear, uncomfortable and can interfere with the wearer's activities.

Resilient earplugs (also known as "slow recovery" earplugs) provide an alternative means of hearing protection against the noise an individual is subjected to. Resilient earplugs can be fabricated from a variety of materials including silicon, various plastics, PVC and polyethylene. Two of the more common materials used are PVC and polyethylene. These materials provide an earplug which can be compressed to a small diameter and inserted into the ear canal. Once in the ear canal, the earplug slowly expands or recovers to seal against the interior surface of the ear canal, thereby inhibiting noise or sound from entering the ear canal.

Pre-insertion shaping of the earplug is typically accomplished by rolling the earplug between the thumb and the index finger. Unfortunately, users frequently fail to roll and compress the earplugs to the proper pre-insertion diameter. When this happens, the earplug will not function to its full potential.

Another problem associated with resilient earplugs occurs when creases are introduced into the outer surface of the earplug as it is being rolled and compressed. Creases introduced during pre-insertion shaping of the earplug can provide a pathway for sound to enter the ear canal, which further reduces the effectiveness of the earplug.

Yet another problem associated with resilient earplugs is that dirt and grime is often transferred from the user's hand to the earplug as it is being handled and shaped prior to insertion. In addition to being unsightly, soiled earplugs have the potential to introduce infectious pathogens into the ear canal. And because of their unsightly appearance, soiled earplugs are often discarded after only one use, which is wasteful.

What is needed, therefore, is an earplug shaping device that enhances the use and effectiveness of resilient earplugs.

BRIEF SUMMARY OF THE INVENTION

The present invention provides a device for pre-insertion shaping of a resilient earplug to a proper diameter without introducing creases in the surface of the plug. The device includes upper and lower structural elements which slidingly engage each another. Both the upper and lower structural elements include a shaping surface. The shaping surfaces oppose one another and are inclined relative to one another. Various embodiments of the present invention also include a slot in communication with a receiver which allows for the shaping of earplugs attached to a cord.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawings (which are not to scale) where:

FIG. 1 is a side view. FIG. 2 is a top view of the device shown in FIG. 1. FIG. 2A is an end view of the device shown in FIGS. 1 and 2. FIG. 3 is a bottom view of the device shown in FIGS. 1, 2 and 2A.

FIGS. 4, 4A, 5, 5A and 6 show a second embodiment of the present invention. FIG. 4 is a side view. FIG. 4A provides an end view. FIG. 5 is a top view. FIG. 5A is a sectional view. FIG. 6 shows a bottom view.

FIGS. 7, 7A, 8, 8A and 9 disclose a third embodiment of the present invention. FIG. 7 is a side view. FIG. 7A shows an end view. FIG. 8 is a top view. FIG. 8A provides a sectional view. FIG. 9 is a bottom view.

DETAILED DESCRIPTION OF THE PREFERRED EMBODIMENT(S)

Figure 2:
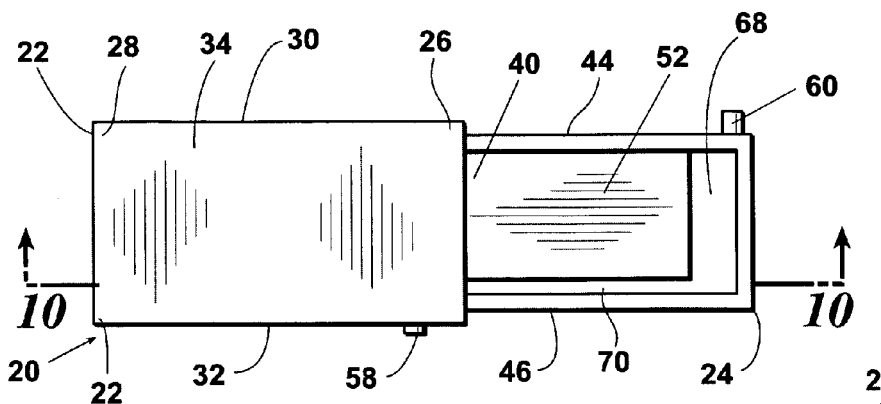
FIGS. 1, 2, 2A and 3 show one embodiment of the present invention.
Figure 2A:
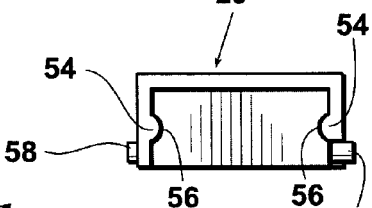

Preferred embodiments of the present invention will now be described with reference to the accompanying drawings, wherein like reference characters designate like or similar parts throughout. The terminology used herein is intended to be interpreted in its broadest reasonable manner, even though it is being utilized in conjunction with a detailed description of certain specific preferred embodiments of the present invention. This is further emphasized below with respect to some particular terms used herein. Any terminology intended to be interpreted by the reader in any restricted manner will be overtly and specifically defined as such in this specification.

Figure 1:
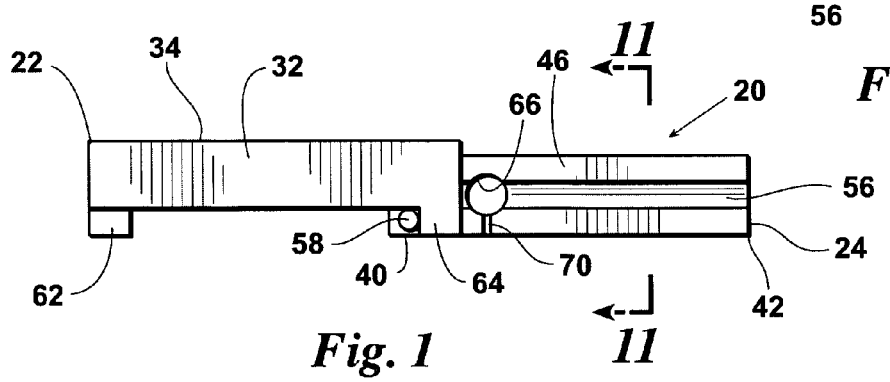
Figure 3:
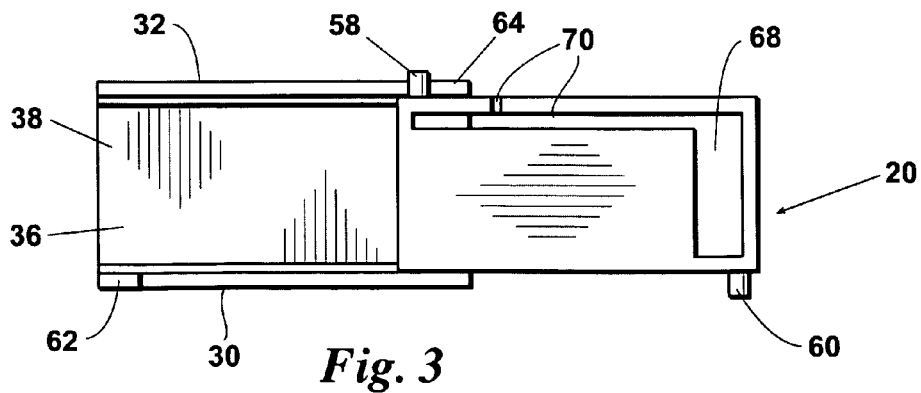

FIGS. 1 through 3 illustrate a resilient earplug shaper 20 according to a preferred embodiment of the invention. Earplug shaper 20 includes an upper structural element 22 and a lower structural element 24. Upper structural element 22 includes a first end 26 in opposed relation to a second end 28, a first side 30 in opposed relation to a second side 32, and a top 34 in opposed relation to a bottom 36. A shaping surface 38 is provided along the bottom 36 of upper structural element 22.

Upper and lower structural elements 22 and 24 may be fabricated from a variety of materials, including wood, metal, plastic and composite materials. In a preferred embodiment, elements 22 and 24 are molded from a lightweight plastic or polymer.

Lower structural element 24 includes a first end 40 in opposed relation to a second end 42, a first side 44 in opposed relation to a second side 46, and a top 48 in opposed relation to a bottom 50. A shaping surface 52 is provided along the top 48 of lower structural element 24.

The upper structural element 22 slidingly engages the lower structural element 24. Preferably, this is achieved by a sliding mechanism that includes a pair of rails 54 and grooves 56 formed in the sides 30, 32, 44 and 46 of the upper and lower structural elements 22 and 24. As shown in FIGS. 1 through 3, each of the interior surfaces of the first and second sides 30 and 32 of upper structural element 22 include a rail 54 which slidingly engages a corresponding groove 56 located on the exterior surface of the first and second sides 44 and 46 of lower structural element 24.

Upper structural element 22 is captured to lower structural element 24 along the rail and grooves 54 and 56 by a first stop 58 located near the first end 40 on one of the two sides 44 and 46 of lower structural element 24. A second stop 60 is located near the second end 42 of lower structural element 24 on the opposing side 46 to the first stop 58. Upper structural element 22 includes a first tab 62 located near the first end 26 of the upper structural element 22 on the corresponding side 44 to the second stop 60. A second tab 64 is located near the second end 28 of upper structural element 22 on the side 32 corresponding to the first stop 58 of lower structural element 24. The first tab 62 engages the second stop 60 to prevent upper structural element 22 from disengaging from lower structural element 24. Likewise, the second tab 64 engages the first stop 58 to prevent upper structural element 22 from disengaging from lower structural element 24. Preferably, upper and lower structural elements are configured to be quickly detached from each other to facilitate cleaning of the earplug shaper 20.

Lower structural element 24 also includes a port 66 in the form of a through opening which passes through either the first or second side 44 or 46 near the first end 26. A receiver 68 located near the second end 42 of lower structural element 24 is in communication with the top 48 and bottom 50 of lower structural element 24. An optional slot 70 passing through lower structural element 24 and in communication with both the port 66 and the receiver 68 facilitates shaping of corded earplugs.

Figure 10A:
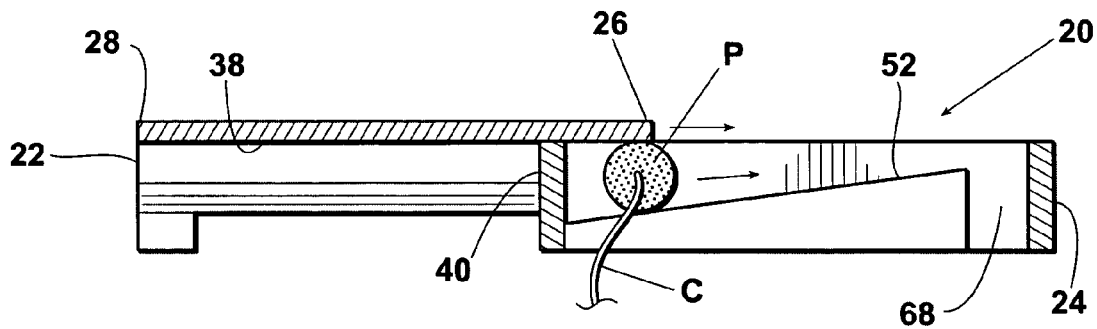
FIGS. 10A, 10B and 10C show a cross-sectional view of the embodiment found in FIGS. 1 through 3 in use rolling an earplug attached to a cord.
Figure 10B:
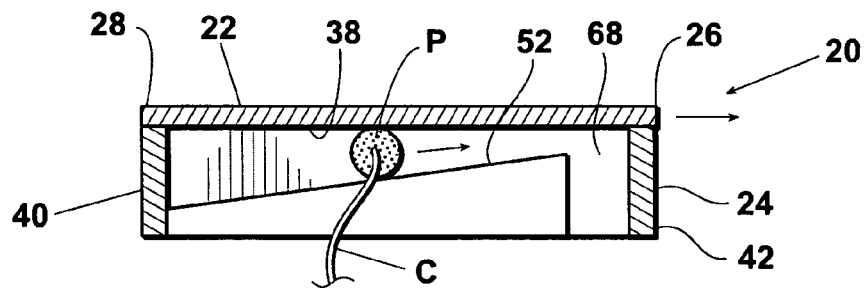
Figure 10C:
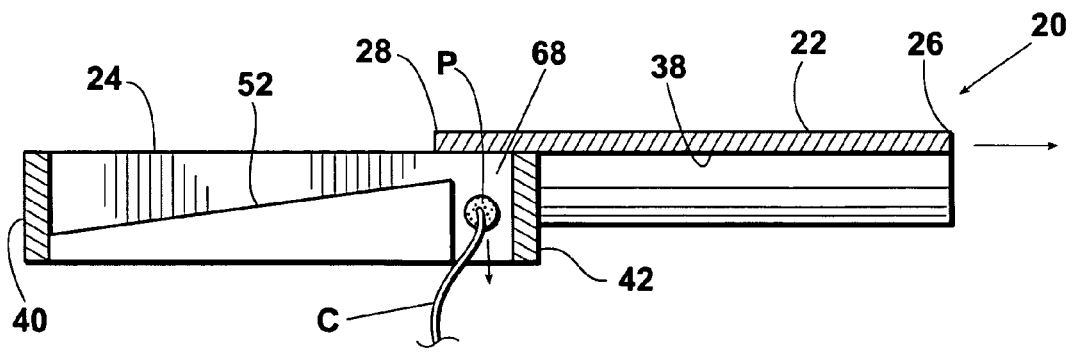

With reference to FIGS. 10A, 10B and 10C, in use a resilient earplug P is inserted into the earplug shaper 20 through the port 66 such that it is captured between the two opposing shaping surfaces 38 and 52. A cord C attached to earplug P is allowed to drop through the slot 70. Upper structural element 22 and lower structural element 24 begin in a starting position as shown in FIG. 10A with the first end 26 of upper structural element 22 adjacent the first end 40 of lower structural element 24. The upper and lower structural elements 22 and 24 are slid relative to one another to an intermediate position as shown in FIG. 10B and then to a final position as shown in FIG. 10C where the second end 28 of upper structural element 22 is adjacent the second end 42 of lower structural element 24. As the upper structural element 22 and lower structural element 24 move relative to one another, earplug P is captured between the opposing shaping surfaces 38 and 52 and is rolled and compressed in diameter from the first ends 26 and 40 of the upper and lower structural elements 22 and 24 to the second ends 28 and 42. As the earplug P is rolled along the shaping surfaces 38 and 52, the cord C is moved through slot 70. If desired, shaping surfaces 38 and 52 may be rough textured (such as 600 grit) to facilitate rolling and shaping of the earplug P between the surfaces 38 and 52. When the earplug P reaches the receiver 68, it has been compressed and its diameter has been reduced. The shaped earplug P is then removed from the receiver 68 and inserted into the user's ear canal where the earplug P slowly expands to a diameter or other dimension that approximates the contour of the user's ear canal.

It will be appreciated that an earplug shaper 20 of the type described herein provides a number of benefits over the prior art method of shaping the earplug by rolling it between the thumb and index finger. For example, the earplug shaper 20 consistently produces a perfectly shaped earplug compressed to the exact diameter recommended, without creases, for maximum sound blockage. Since the user is not required to hand roll the earplug, less dirt and other matter is transferred from the user's hands to the earplug during pre-insertion shaping. Thus, users are more likely to re-use the unsoiled earplug and less likely to develop infections from soiled earplugs.

In an alternative embodiment shown in FIGS. 4, 5, 5A and 6, an earplug shaper 120 includes an upper structural element 122 and a lower structural element 124. The upper structural element 122 includes a first end 126 in opposed relation to a second end 128, a first side 130 in opposed relation to a second side 132, and a top 134 in opposed relation to a bottom 136. A shaping surface 138 is provided along the bottom 136 of upper structural element 122.

Lower structural element 124 includes a first end 140 in opposed relation to a second end 142, a first side 144 in opposed relation to a second side 146, and a top 148 in opposed relation to a bottom 150. A shaping surface 152 is provided along the top surface 148 of lower structural element 124.

Upper structural element 122 slidingly engages the lower structural element 124 preferably in the same manner as described above in connection with the embodiment of FIGS. 1 through 3 where corresponding rails 154 and grooves 156 are formed in the sides 128, 130, 144 and 146 of the upper and lower structural elements 122 and 124. This is best seen in FIG. 4A.

Likewise, upper structural element 122 is captured to lower structural element 124 by a pair of first and second stops 158 and 160 which interact with opposing first and second tabs 162 and 164 to maintain sliding engagement of elements 122 and 124.

Upper structural element 122 includes a receiver 168 located near the second end 128. The receiver 168 is in communication with the top 134 and bottom 136 of upper structural element. An optional slot 170 formed along the top 134 of upper structural element 122 facilitates shaping of corded earplugs.

In use, a resilient earplug is positioned on top 148 adjacent first end 140 of lower structural element 124 with the upper and lower structural elements 122 and 124 in their starting positions as shown in FIG. 5. The upper and lower structural elements 122 and 124 are slid relative to one another to shape the earplug for insertion into a user's ear canal. If the earplug is corded, the cord is moved through slot 170 so that the cord does not interfere with the shaping action of shaping surfaces 138 and 152.

In a further alternate embodiment shown in FIGS. 7, 8, 8A and 9, an earplug shaper 220 includes an upper structural element 222 and a lower structural element 224. The upper structural element 222 includes a first end 226 in opposed relation to a second end 228, a first side 230 in opposed relation to a second side 232, and a top 234 in opposed relation to a bottom 236. A shaping surface 238 is provided along the bottom 236 of upper structural element 222.

Lower structural element 224 includes a first end 240 in opposed relation to a second end 242, a first side 244 in opposed relation to a second side 246, and a top 248 in opposed relation to a bottom 250. A shaping surface 252 is provided along the top 248 of lower structural element 224. The two shaping surfaces 238 and 252 oppose one another and are inclined relative to one another.

As with the above described embodiments shown in FIGS. 1-6, the upper structural element 222 and the lower structural element 224 are slidingly engaged with one another. This is achieved by the use of a pair of interlocking rails 254 and grooves 256 formed in the sides 228, 230, 244 and 246 of the upper and lower structural elements 222 and 224 as best seen in FIG. 7A. Likewise, upper structural element 222 is captured to lower structural element 224 along the rails and grooves 254 and 256 in essentially the same manner as described above by use of stops 258 and 260 and opposing tabs 262 and 264.

With continued reference to FIGS. 7 through 9, earplug shaper 220 includes a receiver 268 located in the upper structural element 222. The receiver 268 is a rectangular portion removed from the second end 228 of upper structural element 222.

Figure 11:
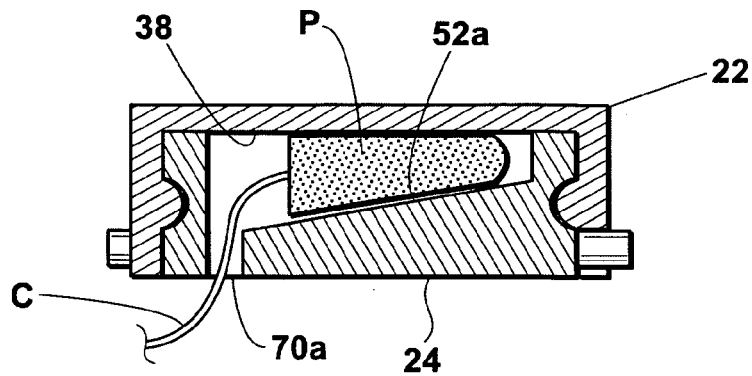
FIGS. 11, 12 and 13 show sectional views of the embodiment shown in FIGS. 1 through 3 with various profiles of the shaping surface.
Figure 12:
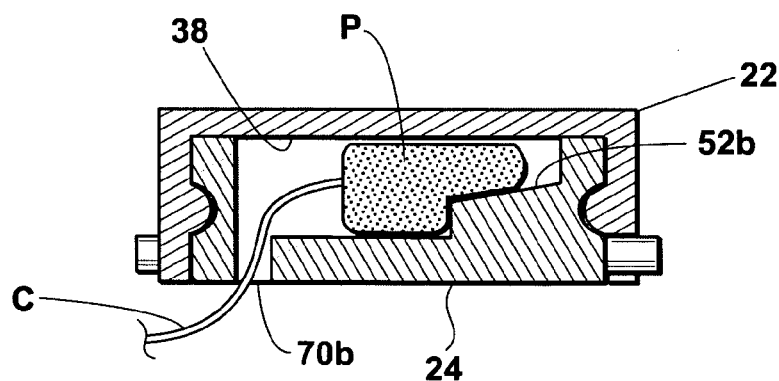
Figure 13:
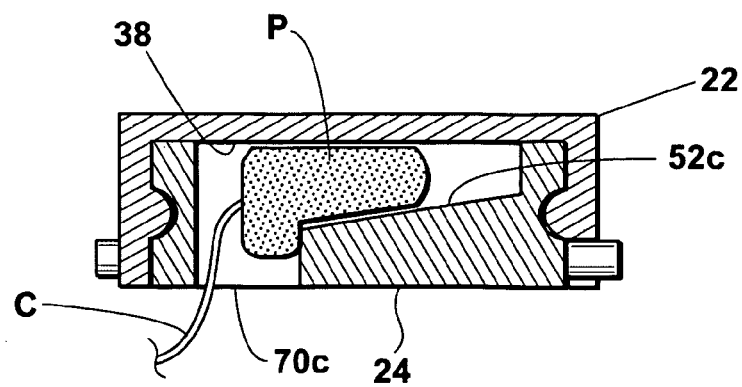

The shaping surfaces for the various embodiments of the earplug shaper described herein can be configured in various ways. FIGS. 11 through 13, all of which are taken along section line 11-11 of FIG. 3, show three such configurations which may be used to shape earplugs that are not corded as well as earplugs that have an attached cord C. The configuration of FIG. 11 differs from that shown in FIGS. 1 through 3 in that one of the shaping surfaces 52a is canted. This canted shaping surface produces a shaped earplug having a smaller diameter at one end, which is believed to make the shaped earplug easier to handle when a user grasps the earplug by the end with the larger diameter. The larger diameter on one end also helps to prevent the shaped earplug from being inserted too far into the ear canal.

A stepped shaping surface 52b as seen in FIG. 12 can also create a rolled plug with a larger diameter at one end. Likewise, the same effect can be obtained by providing a shaping surface 52c with a widened slot 70c, as seen in FIG. 13. In use, the plug P is placed such that the end of the plug P that is attached to the cord C is not be in contact with one of the two shaping surfaces and thus will not be compressed to the smaller diameter found on the opposing end of the plug P.

The foregoing description details certain preferred embodiments of the present invention and describes the best mode contemplated. It will be appreciated, however, that changes may be made in the details of construction and the configuration of components without departing from the spirit and scope of the disclosure. Therefore, the description provided herein is to be considered exemplary, rather than limiting, and the true scope of the invention is that defined by the following claims and the full range of equivalency to which each element thereof is entitled.

What is claimed is:

1. An apparatus for shaping a resilient earplug to facilitate insertion of the earplug into a user's ear canal, said apparatus comprising:
    an upper structural element having a substantially planar upper element shaping surface for contacting the earplug;
    a lower structural element movably engaged with said upper structural element and having a substantially planar lower element shaping surface for contacting the earplug, the lower element shaping surface being in opposed relation to the upper element shaping surface; and
    an interlocking channel and rail slidingly securing the upper structural element to the lower structural element, wherein at least one of said lower element shaping surface and said upper element shaping surface is inclined relative to the other shaping surface, and wherein the earplug is compressed between the lower element shaping surface and the upper element shaping surface as one or both of the shaping surfaces move in relation to the other shaping surface.

2. The earplug shaping apparatus of claim 1 wherein at least one of the shaping surfaces is stepped.

3. The earplug shaping apparatus of claim 1 wherein the interlocking channel is disposed on the lower structural element and the rail is disposed on the upper structural element.

4. The earplug shaping apparatus of claim 1 further comprising said upper structural element being captured relative to said lower structural element.

5. The earplug shaping apparatus of claim 1, wherein each of said upper and lower structural elements further comprise:
    a first end in opposed relation to a second end;
    a first side in opposed relation to a second side; and
    a top in opposed relation to a bottom;
    wherein the upper element shaping surface is adjacent the bottom of the upper structural element and the lower element shaping surface is adjacent the top of the lower structural element.

6. The earplug shaping apparatus of claim 5 further comprising a receiver.

7. The earplug shaping apparatus of claim 6, wherein said receiver includes a passageway in communication with the top of the upper structural element and the bottom of the upper structural element.

8. The earplug shaping apparatus of claim 7 further comprising a slot in communication with the receiver, the top of the upper structural element and the bottom of the upper structural element.

9. The earplug shaping apparatus of claim 6, wherein said receiver includes a passageway in communication with the second end of the upper structural element, the top of the upper structural element and the bottom of the upper structural element.

10. The earplug shaping apparatus of claim 6, wherein said receiver includes a passageway in communication with the top of the lower structural element and the bottom of the lower structural element.

11. The earplug shaping apparatus of claim 10 further comprising:
    a port passing through one of the first or second sides of the lower structural element; and
    a slot in communication with the top of the lower structural element, the bottom of the lower structural element, the port and the receiver.

12. The earplug shaping apparatus of claim 1 wherein each of said upper and lower element shaping surfaces is textured.

13. An apparatus for shaping a resilient earplug to facilitate insertion of the earplug into a user's ear canal, said apparatus comprising:
    an upper structural element having a first end in opposed relation to a second end, a first side in opposed relation to a second side, and a top in opposed relation to a bottom and a non-tubular upper element shaping surface adjacent the bottom of the upper structural element;
    a lower structural element having a first end in opposed relation to a second end, a first side in opposed relation to a second side, and a top in opposed relation to a bottom and a non-tubular lower element shaping surface adjacent the top of the lower structural element;

a receiver in communication with the lower element shaping surface and the bottom of the lower structural element;

a port which passes through either the first or second side of the lower structural element; and a slot in communication wit the lower element shaping surface, the bottom of the lower structural element, the port and the receiver;

wherein the lower structural element is movably engaged with the upper structural element and the lower element shaping surface is in opposed relation to the upper element shaping surface, and at least one of said lower element shaping surface and said upper element shaping surface is inclined relative to the other shaping surface, and wherein the earplug is compressed between the lower element shaping surface and the upper element shaping surface as one or both of the shaping surfaces move in relation to the other shaping surface.

14. An apparatus for shaping a resilient earplug to facilitate insertion of the earplug into a user's ear canal, said apparatus comprising:

an upper structural element having a substantially non-tubular upper element shaping surface for contacting the earplug;

a lower structural element movably engaged with the upper structural element and having a substantially non-tubular lower element shaping surface for contacting the earplug, the lower element shaping surface being in opposed relation tote upper element shaping surface; and an interlocking channel and rail slidingly securing the upper structural element to the lower structural element, wherein at least one of the lower element shaping surface and the upper element shaping surface is inclined relative to the other shaping surface, and wherein the earplug is compressed between the lower element shaping surface and the upper element shaping surface as one or both of the shaping surfaces move in relation to the other shaping surface.

* * * * *

UNITED STATES PATENT AND TRADEMARK OFFICE
CERTIFICATE OF CORRECTION

PATENT NO.       : 7,614,867 B2                               Page 1 of 1
APPLICATION NO.  : 11/391051
DATED            : November 10, 2009
INVENTOR(S)      : Daniel R. Schumaier It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 720 days.

Signed and Sealed this

Nineteenth Day of October, 2010

David J. Kappos
*Director of the United States Patent and Trademark Office*